(12) United States Patent
Zhang

(10) Patent No.: US 8,492,113 B2
(45) Date of Patent: Jul. 23, 2013

(54) MEASUREMENT OF PROTEIN USING INCLUSION BODY DRY WEIGHT

(75) Inventor: Roujian Zhang, Belle Mead, NJ (US)

(73) Assignee: Amgen Inc., Thousand Oaks, CA (US)

( * ) Notice: Subject to any disclaimer, the term of this patent is extended or adjusted under 35 U.S.C. 154(b) by 299 days.

(21) Appl. No.: 12/667,665

(22) PCT Filed: Jul. 9, 2008

(86) PCT No.: PCT/US2008/069529
§ 371 (c)(1),
(2), (4) Date: Oct. 15, 2010

(87) PCT Pub. No.: WO2009/006643
PCT Pub. Date: Jan. 8, 2009

(65) Prior Publication Data
US 2011/0045527 A1   Feb. 24, 2011

Related U.S. Application Data

(60) Provisional application No. 60/947,800, filed on Jul. 3, 2007.

(51) Int. Cl.
*C12Q 1/06* (2006.01)
*C07K 14/00* (2006.01)

(52) U.S. Cl.
USPC .............................. 435/39; 435/69.1; 530/350

(58) Field of Classification Search
USPC .................................... 435/39, 69.1; 530/350
See application file for complete search history.

(56) References Cited

U.S. PATENT DOCUMENTS

| | | | |
|---|---|---|---|
| 4,511,503 A | 4/1985 | Olson et al. | |
| 4,512,922 A | 4/1985 | Jones et al. | |
| 4,518,526 A | 5/1985 | Olson | |
| 5,605,691 A | 2/1997 | Carroll | |
| 5,986,048 A | 11/1999 | Rubroder et al. | |
| 6,632,426 B2 | 10/2003 | Osslund | |
| 6,759,215 B1 | 7/2004 | Zsebo et al. | |
| 6,936,699 B2 | 8/2005 | Peters | |

OTHER PUBLICATIONS

Blum et al., DnaK-mediated alterations in human growth hormone protein inclusion bodies. *Bio/Technology*, 10: 301-4 (1992).
Bowden et al., Structure and morphology of protein inclusion bodies in *Escherichia coli. Bio/Technology*, 9: 725-30 (1991).
Bruggenman et al., Pseudomonas exotoxin fusion proteins are immunogens for raising antibodies against P-glycoprotein. *Biotechniques*, 10: 202-9 (1991).
Marston et al., The prufication of eukaryotic polypeptides synthesized in *Escherichia coli. Biochem. J.*, 240: 1-12 (1986).
Rudolph et al., In vitro folding of inclusion body proteins. *FESEB J.* 10: 49-56 (1996).
Schein et al., Production of soluble recombinant proteins in bacteria. *Bio/Technology*, 7: 1141-9 (1989).
Schoemaker et al., Examination of calf prochymosin accumulation in *Escherichia coli*: Disulphide linkages are a structural component of prochymosin-containing inclusion bodies. *EMBO J.* 4: 775-80 (1985).
Studier et al., Use of T7 RNA polymerase to direct expression of cloned genes. *Methods Enzymol.* 185: 60-89 (1990).
Gross-Selbeck et al., Fast quantification of recombinant protein inclusion bodies with intact calls by FT-IR spectroscopy, *Biotechnol. Prog.*, 23: 762-6 (2007).
Clementschitsch et al., Sensor combination and chemometric modeling for improved process monitoring in recombinant *E. coli* fed-batch cultivations. *J. Biotechnol.*, 120(2): 183-96 (2005).
Cueto-Rojas et al., Interferon-A 2B quantification in inclusion bodies using reversed phase-ultra performance liquid chromatography (RP-UPLC). *J. Chromatogr. B*, 878(13-14): 1019-23 (2010).
Search Report and Written Opinion issued in connection with Singapore Patent Application No. 201000620-3, mailed Oct. 29, 2012.

*Primary Examiner* — Chih-Min Kam
(74) *Attorney, Agent, or Firm* — Marshall, Gerstein & Borun LLP

(57) ABSTRACT

The present invention is directed to improved methods for efficiently producing recombinant proteins. More specifically, the invention relates to a process for calculating the protein in inclusion bodies before the refolding step in large scale recombinant protein production, thereby improving the efficiency of the refolding step and overall yield and quality of the sample protein.

6 Claims, No Drawings

MEASUREMENT OF PROTEIN USING INCLUSION BODY DRY WEIGHT

This application is a 35 U.S.C. 371 national phase application of PCT/US2008/069529, filed Jul. 9, 2008, which claims the priority benefit of U.S. Provisional Patent Application No. 60/947,800, filed Jul. 3, 2007.

FIELD OF THE INVENTION

The present invention relates to methods of measuring protein product from recombinant protein production based on the dry weight of an inclusion body harvest.

BACKGROUND OF THE INVENTION

High level expression of recombinant proteins produced in bacteria, such as *E. coli*, often results in formation of insoluble aggregates within the bacterial cell, known as inclusion bodies (Shein et al., Bio/Technology 7:1141-49, 1989). An inclusion body protein is one that is, in general, overexpressed in the host, which at later stages of expression or purification is visible by phase contrast microscopy as a precipitate. Inclusion bodies are electron-dense amorphous particles which have a discrete border to the cytoplasm but are not surrounded by a membrane (Schoemaker et al., EMBO J. 4:775-780, 1985). During the preparation of inclusion bodies, various types of interactions may lead to secondary adsorption of other contaminants such as, endotoxins, cell wall debris, and lipids (Marston FAO, Biochem. J. 240:1-12, 1986). The average particle size of inclusion bodies is dependent on the particular target protein expressed, the host strain, the expression system and the culture medium used and may be in the range from 0.07 µm for human growth hormone (Blum P et al., Bio/Technology 10: 30)-304, 1992) to 1.5 µm for β-lactamase (Bowden et al., Bio/Technology 9: 725-730, 1991). A further description of inclusion body can be found in U.S. Pat. No. 4,512,922, which refers to inclusion bodies as "refractile bodies."

Inclusion bodies are generally harvested from cell lysate through several centrifugation and wash steps after the cells are lysed (e.g., by lysis by lysozyme, ultrasound treatment or high pressure homogenization). See, for example, U.S. Pat. Nos. 4,511,503; 4,518,526; 5,605,691; and 6,936,699. The purified inclusion bodies are then dissolved or denatured, with, e.g., a detergent or other solution (urea. SDS, guanidine hydrochloride), which causes the insoluble protein molecules to unfold and become soluble. The denaturant may subsequently removed, for example, by dialysis, by molecular sieve, or by centrifugation at high speed to remove higher molecular weight components and decant the denaturant. The recombinant protein is then isolated and refolded to form correct high order structures which are biologically active.

In order to insure the most efficient refolding reaction, it is important to control the amount and concentration of the proteins in the refolding reaction. The protein recovered from the inclusion bodies is typically determined by high performance liquid chromatography (HPLC) analyses of an aliquot of the inclusion body harvest. However, real-time analysis by HPLC methods are complex and time-consuming nature of the process.

Thus, there remains a need in the art for more efficient and accurate methods of determining recombinant protein levels produced during recombinant protein production.

SUMMARY OF THE INVENTION

The present invention is directed to improved methods for measuring the protein produced and shuttled to inclusion bodies in recombinant protein (bacterial) cultures.

In one aspect, the invention provides a method for calculating recombinant protein concentration in bacterial inclusion body (IB) harvests comprising the step of multiplying total concentration of dry solids in an aliquot of an IB harvest slurry and a protein productivity conversion factor (PPCF) in a formula wherein the product of the formula provides total recombinant protein concentration in said aliquot of said IB harvest slurry, and wherein the PPCF for said recombinant protein is determined from an aliquot of an IB harvest slurry by multiplying the ratio of recombinant protein in said aliquot to total dry solids in said aliquot by 1000. The total recombinant protein may be calculated according to the formula:

[(total dry solid,mg)/(IB harvest slurry aliquot,g)× PPCF]×total IB harvest slurry weight,g=(total recombinant protein,mg).

The protein productivity conversion factor may be calculated according to the formula:

(PPCF)=[recombinant protein(mg)in said aliquot/total dry solids in said aliquot(mg)]×1000.

In an alternative embodiment, the conversion factor may be calculated based on alternative units to be determined. For example, concentrations may be expressed as g/kg, g/L, mg/g, mg/ml, and are generally equivalent since the densities of the material are very close to one. As such, a concentration in mg/ml is equivalent to mg/g, assuming the density is close to 1 g/ml.

In one aspect, the recombinant protein may be any protein that is expressed in bacteria in the form of insoluble inclusion body in transformed bacteria, i.e., bacteria which have been transformed or transfected with recombinant DNA vectors that direct the expression of genes coding for heterologous proteins. Recombinant proteins contemplated for use in the method of the invention include, but are not limited to, an antibody (such as a polyclonal antibody, a monoclonal antibody, a human antibody, a humanized antibody, Fab, $F(ab')_2$; Fv; Sc Fv or SCA antibody fragment, bispecific antibody, diabody, peptibody, chimeric antibody; and linear antibody), an enzyme, a hormone, a cytokine, a chemokine, a growth factor, a transcription factor, a transmembrane protein, a cell-surface receptor, a cell-adhesion protein, a cytoskeletal protein, a fusion protein, or a fragment or analog of any of the above proteins.

In one embodiment, the PPCF for one inclusion body harvest aliquot is used to calculate recombinant protein concentration from different fermentation inclusion body harvests carried out following the same protocol.

In another aspect, the invention contemplates that the total recombinant protein in said aliquot of inclusion body harvest slurry is first determined by HPLC assay. In one embodiment, the titer of protein is determined after solubilization of the inclusion bodies in an inclusion harvest aliquot and the recombinant protein in the sample is determined by HPLC analysis.

In a further aspect, the inclusion bodies within the inclusion harvest aliquot are not solubilized before drying.

The invention further contemplates that the dry weight of the inclusion body aliquot is calculated by drying the isolated inclusion body slurry via microwave radiation. In one embodiment, the drying further comprises use of heat. In a further embodiment, the drying is performed on a CEM Lab-Wave 9000. It is further contemplated that the dry weight of the recombinant protein may be determined using techniques common in the art, including heating, microwave radiation, air drying, lyophilization, freeze-drying, and vacuum drying. Once the sample is dried, the dry weight of the solid may be measured using a standard balance mechanism.

DETAILED DESCRIPTION

The present invention is directed to improved methods for determining the protein produced and shuttled to inclusion bodies in recombinant protein host cell cultures.

As disclosed herein, it has been discovered that, under the same or essentially identical fermentation conditions, inclusion body formation is essentially an ordered process and the recombinant protein composition of inclusion bodies is very consistent. Having discovered this consistency of inclusion body formation and composition, a method was proposed and verified to determine recombinant protein concentration in inclusion bodies by measuring the dry weight, or percent solids, of an inclusion body harvest slurry and then multiplying this dry weight measurement by a pre-determined conversion factor. Relying on the consistency of inclusion body composition, the method determines recombinant protein concentration in only a small aliquot of an inclusion body harvest to calculate the protein-specific conversion factor, and eliminates the need to measuring protein in the entire inclusion body harvest using time-consuming and complex methods such as HPLC. Once a fermentation process is designed and established for producing a given recombinant protein in a given host cell, the conversion factor for that protein can be used to extrapolate total recombinant protein for different inclusion body batch harvests without the need to perform the calculation for every batch, as long as the fermentation process remains essentially unchanged. This finding offers a fast, robust and less expensive way of controlling the amount/concentration of proteins before key process steps such as refolding. Additionally, the pre-determined conversion factor can be used to monitor fermentation process consistency.

The term "recombinant protein" refers to a heterologous protein molecule which is expressed in host cells transfected with a heterologous DNA molecule.

The term "inclusion body" refers to an insoluble aggregate within the bacterial host cell which contains protein that is expressed in the host cell. While protein in inclusion bodies in transfected host cells is largely recombinant (heterologous) protein, endogenous (or homologous) host cells proteins can make up a portion of the total protein.

The term "inclusion body harvest" refers to the collected inclusion bodies produced during a fermentation process for production of a recombinant protein. The inclusion body harvest may have varying degrees of purification. Post Kill samples refers to a sample of the bacterial culture before lysis, but after killing of the bacteria using techniques known in the art. Cell Paste refers to a sample of the inclusion body harvest collected, typically by centrifugation, before lysing the bacterial host cells to release the inclusion bodies. The washed inclusion body (WIB) portion refers to an inclusion body harvest after washing the inclusion bodies at least one time, or two times (double washed inclusion body, DWIB).

The term "inclusion body slurry" or "inclusion body harvest slurry" refers to the inclusion body harvest which contains the volume of the inclusion body pellet and any residual volume remaining after collection of the inclusion body, e.g., by centrifugation and decanting of the supernatant. An inclusion body slurry may comprise a resuspended or partially resuspended inclusion body pellet in water.

The term "dry weight" refers to the weight of an inclusion body slurry aliquot after all liquid has been removed from the sample, either by microwave, heating or other techniques known in the art. The dry weight may also refer to the total inclusion body solids or weight of the recombinant protein, based on the percent of recombinant protein in the inclusion body solid.

The term "percent solids" refers to the amount of solids in an inclusion body harvest slurry aliquot after drying the sample and removing all liquid in the sample.

The term "protein productivity conversion factor" (PPCF) refers to a number specific for a recombinant protein being purified from an inclusion body harvest under specific fermentation conditions, and is proportional to the ratio of the weight of recombinant protein in a sample relative to the total inclusion body dry sold weight in the same sample. This protein productivity conversion factor allows determination of the total recombinant protein recovered from the inclusion body harvest. In one aspect, a protein productivity conversion factor is determined by HPLC assay. The PPCF is calculated by the formula:

PPCF=[(total recombinant protein in a IB harvest aliquot,mg)/(total dry solids in the same IB harvest aliquot,mg)]×1000.

The term "total recombinant protein concentration" refers to the total protein recovered from a fermentation process, based on the weight of recombinant protein in inclusion bodies in the total weight of dry solids of the inclusion body harvest. Total recombinant protein may be calculated using the following formula:

[(total dry solid,mg)/(IB harvest slurry aliquot,g)× PPCF]×total IB harvest slurry weight(g)=(total recombinant protein,mg).

The present invention is useful to determine the protein productivity conversion factor for any recombinant protein that is produced in a designed fermentation process. Recombinant proteins contemplated for use in the method of the invention include, but are not limited to, an antibody (such as a polyclonal antibody, a monoclonal antibody, a human antibody, a humanized antibody, a Fab, $F(ab')_2$, Fv; Sc Fv or single chain antibody fragment, a bispecific antibody, a diabody, a peptibody, a chimeric antibody; and a linear antibody), an enzyme, a hormone, a cytokine, a chemokine, a growth factor, a transcription factor, a transmembrane protein, a cell-surface receptor, a cell-adhesion protein, a cytoskeletal protein, a fusion protein, or a fragment or analog of any of the above proteins.

Purification and Isolation of Inclusion Bodies

Techniques for isolating inclusion bodies, purifying recombinant protein from inclusion bodies, and techniques for refolding or renaturing protein are well known to those skilled in the art. For example, see Sambrook, J. et al., Molecular Cloning: a Laboratory Manual, pp. 17.37-17.41, Cold Spring Harbor Laboratory Press (1989); Rudolph, R. et al., FASEB J. 10:49-56 (1995).

Purification of the inclusion bodies may be carried out using well-known techniques in the art. See, for example, Ausubel et al., (Current Protocols in Molecular Biology, John Wiley and Sons, New York, N.Y., Ch, 1994). Cells are first centrifuged resulting in a cell pellet. The pellet is then resuspended in an appropriate buffer and the inclusion bodies released by lysing cells under high pressure, sonication, or chemical means, such as addition of lysozyme or denaturing agents. In the present invention, it is contemplated that cells are lysed under conditions that do not lead to solubilization of the inclusion bodies.

For purposes of calculating the PPCF for a protein in a fermentation process, proteins in an aliquot of inclusion body harvest may be solubilized using reagents commonly used in the art, including guanidinium salts, urea, detergents, and other organic solvents (See e.g., U.S. Pat. No. 5,605,691 and Bruggeman et al., Biotechniques 10:202-209 (1991)). It is noted that the efficacy of the solubilizing agent varies with the physical characteristics of the protein. Exemplary guanidinium salts include guanidine-HCl. Exemplary detergents include sodium dodecyl sulfate (SDS), Triton-X, caprylic acid, cholic acid, 1-decanesulfonic acid, deoxycholic acid, glycocholic acid, glycodeoxycholic acid, taurocholic acid, taurodeoxycholic acid, and members of the family of sodium salts of sulfate detergents (e.g., sodium tetradecy) sulfate and sodium hexadecyl sulfate) (see U.S. Pat. No. 5,605,691). These reagents may be used alone or in combination with each other, or other reagents as appropriate for the recombinant protein being purified.

Protein Expression

Inclusion bodies of interest in the present invention are formed by recombinant protein expression in bacterial host strains. Bacterial hosts strains contemplated for use in the invention include *E. coli* strains, including, but not limited to, BL21 (DE3), BL21 (DE3) pLysS, and BL21 (DE3) pLysE (F. W. Studier et al., Methods in Enzymology 185:60-89 (1990)), MC1061, AG1, AB1157, BNN93, BW26434, CGSC Strain #7658, C60, C600 hflA150 (Y1073, BNN102), D1210, DB3.1, DH1, DH5α, DH10B, DH12S, DM1, ER2566 (NEB), HB101, IJ1126, IJ1127, JM83, JM101, JM103, JM105, JM106, JM107, JM108, JM109, JM109(DE3), JM110, JM2.300, LE392, Mach1, MC4100, MG1655 Rosetta (DE3) pLysS, Rosetta-gami (DE3) pLysS, RR1, STBL2, STBL4, SURE, SURE2, TG2, TOP10, Top10F', W3110, XL1-Blue, XL2-Blue, XL2-Blue MRF', XL1-Red, XL10-Gold, XL10-Gold KanR. Other bacterial strains known in the art suitable for recombinant protein production and which form inclusion bodies may be used in the methods of the invention.

Recombinant proteins are expressed in a selected strain according to standard fermentation procedures known in the art. The procedures are adaptable for the bacterial strain being used and the recombinant protein to be expressed. For example, bacterial cultures may be grown to a selected density ($OD_{600}$) of culture, and in an appropriate selection medium prior to harvest of inclusion bodies. See Ausubel et al., (Current Protocols in Molecular Biology, John Wiley and Sons, New York, N.Y., 1994). Methods of recombinant protein production are described in, for example, U.S. Pat. No. 6,759,215 and U.S. Pat. No. 6,632,426.

Determination of Protein in Inclusion Body Harvests

Recombinant protein concentration in an aliquot of an inclusion body harvest can be determined using methods known in the art, including high performance liquid chromatography (HPLC), ion exchange chromatography, Bradford assay, UV absorbance, fluorescent techniques, or Western blot analysis. Of the above methods, the HPLC methods allows for calculation of both protein concentration and purity of the sample in the same test run. As such, in the present invention, in one aspect it is contemplated that the concentration of a protein in a sample is carried out using HPLC.

In order to determine the amount of protein in an aliquot of the fermentation culture and the inclusion body harvest, an HPLC titer is performed. In the HPLC titer, a sample aliquot of the IB harvest is collected, the inclusion bodies solubilized and the protein denatured. The sample is then prepared for HPLC to determine protein purity/concentration in a protein sample using methods and techniques well-known in the art (Current Protocols in Protein Chemistry, John Wiley and Sons, New York, N.Y., 1994), and as described herein. Regardless of how recombinant protein concentration in the IB harvest aliquot is determined, the calculated concentration is then used to determine the protein productivity conversion factor.

Methods for Determining Inclusion Body Dry Weight or Percent Solids

The dry weight or percent solids of the inclusion body harvest may be determined using any method in the art, including heating, microwave radiation, air drying, lyophilization, freeze-drying, and vacuum drying. Once the sample is dried, the dry weight of the solid is measured using a standard balance mechanism.

A combination of heating and microwave radiation is efficient for drying the sample aliquot and determining the percent solids therein. In one aspect, the inclusion body harvest may be dried using microwave radiation and heat. The CEM LabWave 9000 instrument (CEM Corporation, Matthews, N.C.) is designed to reach a Moisture/Solids Range of 0.01% to 99.99% in liquids, solids, and slurries, up to 0.01% resolution. The instrument provides protein output to 0.1 mg readability, and provides microwave power from 0 to 100% of full power (630 watts) in 1% increments. In related embodiment, the inclusion body sample may be dried using other moisture analyzer equipment known in the art, including but not limited to CEM AVC-80 Microwave Moisture Analyzer, CEM Smart System, Denver Instrument M2 Microwave Analyzer (Denver Instruments, Denver, Colo.), Omnimark uWave (Sartorius-Omnimark, Goettingen, Germany), and the Sartorius MMA30 (Sartorius, Goettingen, Germany).

The following examples illustrate various non-limiting embodiments of the invention and/or provide support therefore.

Example 1

Recombinant protein is often expressed in *E. coli* as insoluble inclusion bodies. In the past, inclusion bodies were thought to be a random precipitation of over-expressed recombinant proteins. Recently, however, it has been suggested that inclusion bodies may form in an ordered aggregation process, and if these inclusion bodies were found to have a consistent recombinant protein composition, it may no longer be necessary to quantitate recombinant protein concentration in an inclusion body harvest using complex and time-consuming HPLC methods for every fermentation and inclusion body harvest. Thus, in order to determine if inclusion bodies are produced in an ordered manner having recombinant protein in a consistent composition, initial experiments were designed to attempt formulation of a mathematical model which would allow for quantifying protein content with minimal experimental effort.

At the end of a cell fermentation process for making recombinant human granulocyte colony stimulating factor (r-metHuG-CSF), *E. coli* host cells were lysed using high pressure and inclusion bodies were harvested through multiple centrifugation processes prior to protein solubilization and refolding. This inclusion body broth was then first used for protein concentration analysis.

In order to determine the amount of r-metHuG-CSF protein compared to host protein and other contaminants in the dried sample, the inclusion body "productivity" is determined. Productivity is defined as the ratio between sample protein and total dry weight of the inclusion body sample and this ratio, when multiplied by 1000 provides a protein productivity conversion factor (PPCF) for a desired recombinant protein expressed in a set fermentation process:

$$PPCF=[(\text{total recombinant protein,mg})/(\text{total dry solids,mg})]\times 1000.$$

In determining this ratio. RP-HPLC was carried out using an aliquot of the IB harvest slurry. A portion of the IB harvest slurry was suspended by vortexing in a tube or stirring in a beaker, and 1 mL of the suspension broth was added to 30 mL of incubation/denaturation buffer (8 M Guanidine HCl, 50 mM Tris, 5 mM EDTA, 50 mM D 11, pH 8.4±0.1). The mixture was incubated in a water bath at 65±3° C. for approximately 30 minutes, after which 40 µL of the denatured and reduced r-metHuG-CSF was injected onto a 4.6×100 mm POROS R1/10 column (Applied Biosystems, Foster City, Calif.) on an Agilent 1100 HPLC (Agilent, Santa Clara, Calif.). Recombinant protein eluted at approximately 6.2 min under a rapid gradient using 60% mobile phase A [0.1% (v/v) TFA (sequanal grade, Pierce, Rockford, Ill.), 7% (v/v) IPA in water] to 55% mobile phase B [0.1% (v/v) TFA, 5% (v/v) IPA in acetonitrile (Sigma-Aldrich, St. Louis, Mo.)] over 9 minutes at a flow rate of 2 mL/min. Throughout the analysis, an on-line UV detector set at 214 nm was used to quantify the protein peak. The r-metHuG-CSF protein content in each sample was calculated from the standard calibration curve constructed by linear regression.

Cell fermentation samples taken prior to cell breakage, such as Post Kill samples and Cell Paste samples, i.e., a sample taken from the cell pellet following centrifugation of the fermentation broth, contain large amount of $E.\ coli$ components, including host cell proteins. HPLC analysis showed that recombinant r-metHuG-CSF protein in Cell Paste averages approximately 29% of the total dry weight of cell paste (Tables 1 and 2). Further analysis also showed that the ratio between $E.\ coli$ host cell proteins and the sample protein in this cell paste is variable, which is reflected by the relatively large variability in Cell Paste Productivity (Tables 1 and 2). Table 1 is a comparison of productivity between Double Washed Inclusion Bodies (DWIB) and productivity in Cell Paste from which the DWIB were obtained. Productivity is expressed as the ratio of sample protein to total dry weight times 100%. Table 2 shows a comparison of Productivity in Washed Inclusion Bodies (WIB) also compared to Cell Paste from which the WIB were obtained.

TABLE 1

|  | Sample 1 | Sample 2 | Difference |
|---|---|---|---|
| Cell Paste Productivity | 26% | 30% | ~14% |
| DWIB Productivity | 68.62% | 66.43% | ~3% |

TABLE 2

| WIB Lot # | WIB Productivity | Cell Paste Lot # | Cell Paste Productivity |
|---|---|---|---|
| xxx418 | 67.13% | xxx657 | 23.9% |
| xxx233 | 67.47% | xxx225 | 29.6% |
| xxx363 | 65.50% | xxx225 | 29.6% |
| xxx232 | 68.27% | xxx225 | 29.6% |
| xxx595 | 69.20% | xxx225 | 29.6% |
|  |  | xxx394 | 30.2% |
| xxxpp1 | 69.46% | xxxsd2 | 26% |
| xxxpp2 | 67.53% | xxxsd0 | 30% |
| xxxpp3 | 63.87% | xxxsd2 | 26% |
| xxxpp5 | 63.17% | xxxsd0 | 30% |
| Average | 66.84% |  | 28.5% |
| RSD | 3.3% |  | 7.9% |

These results and the HPLC analyses show that after the cells are lysed, a majority of the host cell proteins are removed from the inclusion body fraction through the centrifugation steps. The inclusion bodies, washed inclusion bodies and double washed inclusion bodies elute with almost the same profile, with the recombinant r-metHuG-CSF protein demonstrating a tight elution profile. Analysis showed that the recombinant protein accounted for almost 93% of the total protein in the inclusion bodies.

The average recombinant protein productivity increases from 29% in Cell Paste to 67% in Inclusion Bodies. In addition, the variability (RSD) in productivity decreases from 8% in Cell Paste to 3% in Inclusion Bodies (Tables 1 and 2).

With the present invention, in the instances that recombinant proteins form inclusion bodies in an ordered and consistent manner between fermentation harvests, and fermentation is carried out following the same or essentially the same protocol, the protein productivity conversion factor determined for an aliquot of the IB harvest slurry can be used to determine the protein in the other fermentation harvests. For example, once calculated as presented herein, the total protein in a given amount of IB harvest slurry could readily be determined by multiplying the dry solid in the slurry by the PPCF determined above without having to perform HPLC on every IB harvest produced under the same fermentation conditions.

Example 2

In order to determine if the dry weight analysis described above allows for accurate prediction of recombinant protein concentration in an IB harvest, the predicted recombinant protein concentration obtained with dry weight samples as above was compared to the sample concentration as measured using HPLC.

HPLC sample preparation was identical to the titer assay described above wherein 40 µL of a denatured and reduced IB harvest slurry sample was injected onto a 4.6 mm ID×150 mm C4 bonded phase silica column with 5 µm particle diameter and 300 Å pore size (YMC, Shimogyo-ku, Kyoto, Japan) on an Agilent 1100 HPLC (Agilent, Santa Clara, Calif.). The reduced protein mixture was separated under a full gradient using 20% mobile phase A [0.1% (v/v) TFA in water] to 85% mobile phase B [0.1% (v/v) TFA in 90% acetonitrile] over 80 minutes at a flow rate of 0.8 ml/min. Throughout the analysis an on-line UV detector set at 214 nm was used to monitor the protein peaks.

When compared to the traditional HPLC assays, the dry weight assay correlated with the results in the HPLC assay (Table 3). For correlation between the HPCL assay and dry weight assay, 670 was used as the conversion factor.

TABLE 3

| Lot | Dry weight result (mg/mL) | HPLC result (mg/mL) | % difference (Dry weight against HPLC) |
|---|---|---|---|
| xxx001 | 104.16 | 104.56 | −0.4% |
| xxxpp3 | 25.25 | 25.85 | −2.3% |
| xxxpp5 | 16.24 | 16.10 | 0.9% |
| xxxpp6 | 15.82 | 16.45 | −3.8% |
| xxxpp7 | 17.38 | 17.92 | −3.0% |
| xxx776 | 10.50 | 10.09 | 4.1% |
| xxx779 | 10.74 | 10.10 | 6.3% |
| xxx454 | 9.68 | 9.29 | 4.2% |
| xxx780 | 9.83 | 9.96 | −1.3% |
| xxx781 | 9.63 | 9.40 | 2.5% |
| xxx782 | 10.17 | 10.49 | −3.1% |
| xxx458 | 9.95 | 9.79 | 1.6% |
| xxx793 | 10.39 | 9.98 | 4.0% |
| xxx783 | 9.63 | 9.61 | 0.2% |
| xxx784 | 9.70 | 9.78 | −0.9% |
| xxx785 | 8.66 | 9.00 | −3.7% |
| Average |  |  | 0.3% |

The difference between the two assays was a combination of inherent variability, and mainly due to the HPLC assay, since it was a single determination and in general has larger variability. The average difference between these two assays was as small as 0.3%. The accuracy of the dry weight assay is probably within ±3%.

These results demonstrated that the method of determining dry weight of a protein by calculating the protein concentration based on the inclusion body protein content is an accurate and fast method for determining protein concentration before proceeding into the protein refolding steps. Determining the protein concentration using this method saves time needed to prepare an HPLC sample and also money in preparing these samples. Additionally, using the dry weight measurement is an accurate method to determine protein concentration before calculating the reagents necessary for the protein refolding step. Therefore, the present method provides a faster, cheaper method for determining protein concentration in large scale protein production.

Example 3

In order to identify factors that may influence the dry weight assay described above, the assay was performed on IB samples subjected to different preparative steps.

To determine the degree of variability in the inclusion body samples, the r-metHuG-CSF protein concentrations obtained via the new dry weight measurement were compared to those obtained by conventional HPLC measurement. A minor factor on variability was the concentration of the sample. When IB harvest slurry samples are extremely diluted, the weighing variability increases. The dry weight assay was usually performed in duplicate on two instruments for a total of four determinations per sample. The HPLC assay was usually a single determination due to its complexity.

For dry weight and percent solids measurements, inclusion body broth was suspended by vortexing in a tube or stirring in a beaker. Approximately 2 mL of the suspended broth was loaded on to a pre-tared sample pad in a CEM Smart System Solids and Moisture Analyzer, CEM LabWave 9000 (CEM Corporation, Matthews, N.C., USA). The r-metHuG-CSF sample was heated and dried at 100% power level for 5 minutes. Percent Solids is automatically calculated by the instrument.

Results of the comparisons between dry weight measurements are shown in Tables 4 and 5. Table 4 shows the precision of the dry weight assay using frozen samples.

TABLE 4

| Determination | Instrument | Percent Solids | Determination | Instrument | Percent Solids |
|---|---|---|---|---|---|
| 1 | 2 | 3.707% | 2 | 1 | 3.850% |
| 3 | 2 | 3.749% | 4 | 1 | 3.827% |
| 5 | 2 | 3.679% | 6 | 1 | 3.832% |
| 7 | 2 | 3.762% | 8 | 1 | 3.737% |
| Average of Instrument 2 | | 3.724% (n = 4) | Average of Instrument 1 | | 3.812% (n = 4) |
| RSD of Instrument 2 | | 1.0% (n = 4) | RSD of Instrument 1 | | 1.3% (n = 4) |
| Overall Average | | | | | 3.768% (n = 8) |
| Overall RSD | | | | | 1.7% (n = 8) |

The precision of the dry weight was also assayed using fresh samples. Two measurements per lot were performed using two separate instruments for a total of four measurements per lot. The average of the fresh sample measurements in shown in Table 5.

TABLE 5

|  | xxxpp6 | xxxpp7 |
|---|---|---|
| Average | 2.361% (n = 4) | 2.594% (n = 4) |
| RSD | 0.6% (n = 4) | 0.9% (n = 4) |

In general, it was found that the precision of the dry weight assay is impacted by two factors. The major factor is the freshness of the sample; inclusion bodies tend to aggregate upon freeze-thaw or long term storage at 4° C., which leads to sample heterogeneity and higher assay variability.

The results shown above demonstrate that inclusion body dry weight measurements are comparable to those obtained using typical HPLC measurements, and are still accurate whether the IB harvest sample was first frozen or stored at 4° C. Although the percent solids detected may vary due to sample preparation before the measurements, the dry weight measurements are consistent and in-line with those obtained using traditional HPLC protein measurements. Thus, the present invention provides an accurate, efficient method for determining protein concentration in an inclusion body harvest in order to reduce the quantity of sample that needs to be taken before the refolding reaction, thereby increasing the amount that is available for the refold reaction, and also provides better control of the protein input into the refolding step in recombinant protein production, and ultimately improve recombinant protein yield and quality.

Numerous modifications and variations in the invention as set forth in the above illustrative examples are expected to occur to those skilled in the art. Consequently only such limitations as appear in the appended claims should be placed on the invention

What is claimed:

1. A method for measuring recombinant protein concentration in bacterial inclusion body (IB) harvests comprising the steps of
   i) measuring the total weight of dry solids from an aliquot of an inclusion body harvest slurry,
   ii) multiplying total weight of dry solids in the aliquot of an IB harvest slurry using a pre-determined protein productivity conversion factor (PPCF) in a formula, wherein the product of the formula provides total recombinant protein concentration in said aliquot of said IB harvest slurry, and wherein the PPCF for said recombinant protein is calculated in an aliquot of an IB harvest slurry by multiplying the ratio of recombinant protein in said aliquot to total dry solids in said aliquot by 1000, wherein the PPCF for one inclusion body harvest aliquot is used to calculate recombinant protein concentration from different fermentation inclusion body harvests carried out following the same protocol, iii) measuring the total IB harvest slurry weight and the total weight from the aliquot of IB harvest slurry, and iv) multiplying the product of (ii) by the ratio of total IB harvest slurry weight to the total weight from the aliquot of IB harvest slurry, wherein the product of iv) provides the total recombinant protein concentration in the bacterial inclusion body (IB) harvest.

2. The method of claim 1 wherein the total concentration of recombinant protein in said aliquot of IB harvest slurry is first determined by HPLC assay.

3. The method of claim 1 wherein the dry weight of the aliquot of total IB harvest slurry is determined by drying the isolated inclusion body slurry via microwave radiation.

4. The method of claim 3 wherein the drying further comprises use of heat.

5. The method of claim 4 wherein the drying is performed on a CEM LabWave 9000.

6. The method of claim 1 wherein the concentration of recombinant protein in the aliquot in the pre-determined PPCF is measured by High Performance Liquid Chromatography (HPLC).

\* \* \* \* \*

UNITED STATES PATENT AND TRADEMARK OFFICE
CERTIFICATE OF CORRECTION

PATENT NO. : 8,492,113 B2  Page 1 of 1
APPLICATION NO. : 12/667665
DATED : July 23, 2013
INVENTOR(S) : Roujian Zhang It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 587 days.

Signed and Sealed this
Eighth Day of September, 2015

Michelle K. Lee
*Director of the United States Patent and Trademark Office*